United States Patent [19]

Marks

[11] Patent Number: 5,391,877
[45] Date of Patent: Feb. 21, 1995

[54] COMBINED IMAGING SCANNER

[76] Inventor: Michael A. Marks, 2334 Morgan La., Dunn Loring, Va. 22027

[21] Appl. No.: 186,631

[22] Filed: Jan. 26, 1994

[51] Int. Cl.⁶ .............................................. G01T 1/166
[52] U.S. Cl. ........................... 250/363.04; 250/363.03
[58] Field of Search ...................... 250/363.03, 363.04, 250/363.09

[56] References Cited

U.S. PATENT DOCUMENTS

| | | | |
|---|---|---|---|
| 4,150,292 | 4/1979 | Ter-Pogossian | 250/363.03 |
| 5,155,365 | 10/1992 | Cann et al. | 250/363.04 X |
| 5,210,421 | 5/1993 | Gullberg et al. | 250/363.04 |
| 5,289,008 | 2/1994 | Jaszczak et al. | 250/363.04 |

FOREIGN PATENT DOCUMENTS

| | | | |
|---|---|---|---|
| 61-226674 | 10/1986 | Japan | 250/363.04 |
| 9100048 | 1/1991 | WIPO | 250/363.04 |

OTHER PUBLICATIONS

Park et al, "Use of Simultaneous Transmission-Emission Scanning in the Diagnosis of Pericardial Effusion", vol. 13, No. 6, Jour. Nucl. Med. Jun. 1972 pp. 347–348.
Bailey et al., "Improved SPECT Using Simultaneous Emission and Transmission Tomography", vol. 28, No. 5, May 1987, pp. 844–851.
Thompson et al, "Simultaneous Transmission and Emission Scans in Position Emission Tomography", IEEE Nuclear Sci. Sym., Submitted to IEEE Transaction on Nuclear Sci. Feb. 1989, pp. 1–7.

*Primary Examiner*—Constantine Hannaher
*Assistant Examiner*—Edward J. Glick
*Attorney, Agent, or Firm*—William F. Hamrock

[57] ABSTRACT

A combined imaging scanner is disclosed for fusing together image data obtained by a computed tomographic (CT) scanner and a single photon emission computed tomographic (SPECT) scanner. The diagnostic radiology imaging CT Scanner anatomical data provides a background map with which is convolved the radioscope distribution SPECT scanner data to yield a color shaded relief image which can then be printed on a laser film printer or other output device. Both sets of data are collected almost simultaneously while the patient is in a fixed position. The apparatus includes combined gantries supporting both CT and SPECT scanners, a computer, a printer and a table to slip through both gantries while holding the patient in a fixed position.

7 Claims, 1 Drawing Sheet

COMBINED IMAGING SCANNER

BACKGROUND OF THE INVENTION

1. Field of the Invention

This invention relates to combining a single photon emission computed tomographic SPECT scanner with a computed tomographic CT scanner, and more particularly, providing a Combined Single Photon Emission Computed Tomographic CSPECT Scanner which convolves the data obtained from the SPECT scanner with the anatomical data obtained from the CT scanner.

2. Description of the Prior Art

This invention is directed to nuclear medicine imaging equipment. Presently most nuclear medicine studies consist entirely of a plainer imaging procedure. After being injected (usually intravenously) with a radio labeled pharmaceutical the patient is positioned under, in front-of, or on-top-of a nuclear medicine gamma camera (Anger camera). Images are formed in a direct relationship to radionuclide concentration within the body. Very little, if any depth information is retained in the final images. Occasionally, more sophisticated images may be obtained by rotating the camera about the patient, and collecting and analyzing the tracer distribution information by computer. The result is called single photon emission computed tomography (SPECT). Today with the advent of mononuclonal antibody tracers appearing onto the commercial market, an increased number of SPECT imaging procedures are being ordered. The tracer distribution in a given patient may vary widely from anatomical area to anatomical area, and change also with time. Normal physiologic tracer accumulation in large organs like the liver or the bone marrow are used as landmarks to determine where pathophysiologic tracer accumulation accumulates.

For example, a patient with known colon cancer may get injected with a tracer dose of a radiolabeled monoclonal antibody sensitive to both ovarian and colon cancer. SPECT images of the patient are typically obtained immediately and then again 96 hours after injection. Transverse, coronal and sagital SPECT images are usually processed and reviewed by the attending nuclear medicine physician shortly thereafter, in an attempt to determine sights of metastatic disease. Vague anatomic landmarks are provided by normal physiologic tracer accumulation, and are deemed normal. The physical location of the abnormal tracer accumulation is reported relative to normal known organ boundaries. The anatomical information provided by SPECT is poor. The resolution is 1.5–2.0 cm and many normal organ boundaries are not even identified. If the nuclear medicine physician is capable of interpreting computed tomography (CT) images and if the patient had recent CT imaging, the physician might attempt to cross correlate the findings on both studies. Unfortunately, the patient may not have been in the same position for the CT scan as the SPECT scan, or the gantry of the CT scanner may have been at a different angle than was used to do the SPECT study. Ultimately, it is variation in patient position which makes direct mathematical superposition of these studies impossible. Limited crude superposition is now becoming possible using the latest computer techniques. Currently, one can take two similar images, one from CT and one from SPECT, and superimpose them, using sophisticated software on a workstation like the SUN, or a powerful desktop computer. Ultimately, no matter what system is used, final image alignment is done "by eye". Again, one should note that, variation in patient position makes exact superposition unlikely.

Most institutions do not even bother to take the time to superimpose SPECT and CT information. The current state of the art is to view the SPECT image information, and if it is present, also view available CT (or Magnetic Resonance MR) data. One then superimposes these two data sets mentally (in one's head). Obviously this method is less than optimum, and results in significant errors.

Accordingly, it is an object of the present invention to have an imaging device which would obtain the SPECT images and the CT images more or less simuataneously, in a single examination, with the patient in a fixed position.

It is another object to have the SPECT images convolved directly with the anatomical images produced by its own CT scanner.

Other novel features which are characteristic of the present invention will be better understood from the following description considered in connection with the accompanying drawing in which preferred embodiments of the invention are illustrated. It is expressly understood however, that the drawing is for the purpose of illustration and description only and is not intended as a definition of the limits of the invention.

SUMMARY OF THE INVENTION

The basic hardware needed to obtain a CT scan is added to that hardware needed to obtain a SPECT scan. In most cases this will probably result in two separate gantries separated by some small space, but a single combined gantry or a single gantry with a specially equipped detector array might perform the same function. The data obtained for the CT scan is used as a map with which to convolve the radionuclide tracer distribution information, provided by the SPECT scanner portion of the apparatus. Only a single table and a single computer are needed. Once the patient is placed on the scanner table the CT scan and the SPECT scan are performed more or less simultaneously with the patient in a given anatomical position. Since the data is collected by a single device all the variables are controlled and simple mathematical processes are used to convolve the resultant data sets. Using the CT data as a map, the areas of tracer accumulation are shaded to denote the resultant degree of tracer accumulation. Color is used to help make the information easier to interpret. Red could be assigned to those areas of high radiotracer accumulation and blue could be assigned to those areas of weak tracer accumulation. The in-between colors will be divided according to the normal rainbow spectrum, from blue to red, in direct proportion to radiotracer accumulation. This data is used to color the anatomical data provided by CT. The result is a new imaging technology that brings nuclear medicine into the twenty-first century.

The CT data can also be used to provide attenuation correction information to improve the accuracy of the dose distribution and the resultant image information provided by SPECT. This will further improve standard SPECT scans that otherwise might not warrant full CSPECT color fused images (such as cardiac SPECT studies).

DETAILED DESCRIPTION OF SPECIFIC EMBODIMENTS

Figure 1:
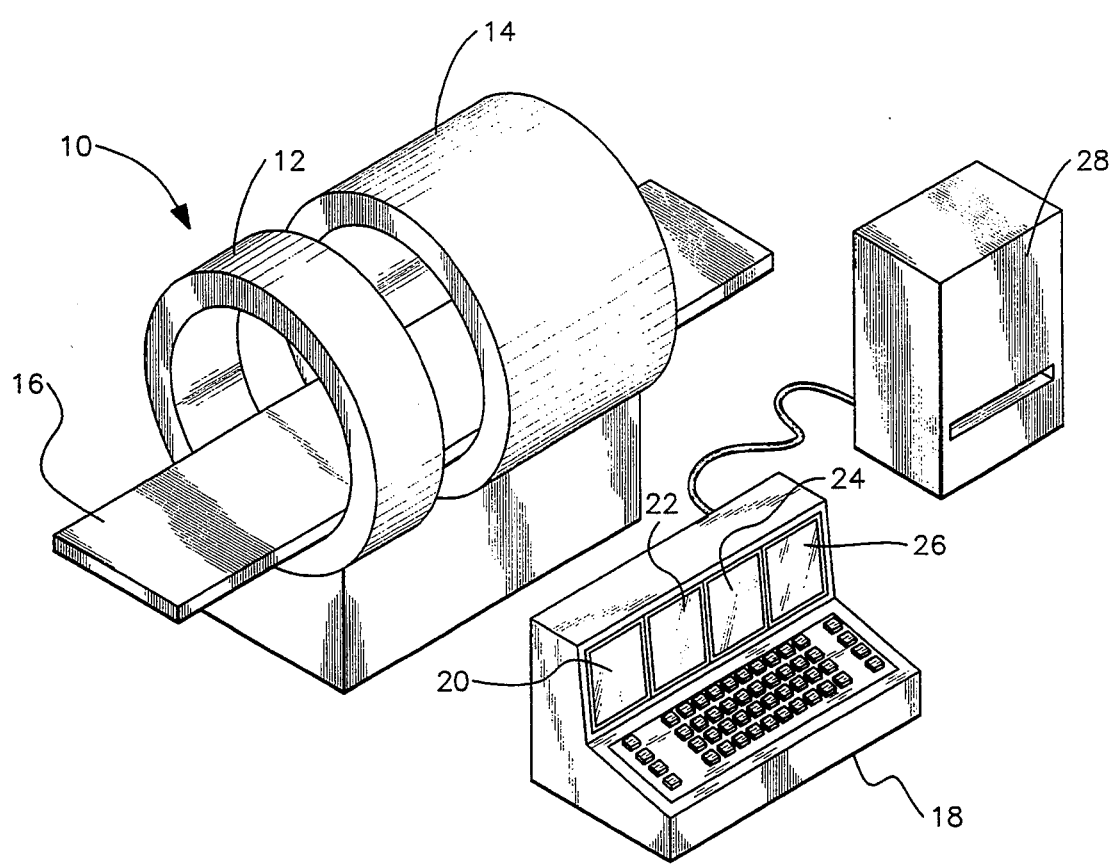
FIG. 1 is a perspective view of a preferred embodiment of the invention.

The Combined Single Photon Emission Computed Tomographic CSPECT Scanner does not merely take two similar images, one from a CT scanner and one from a SPECT scanner, and compare them one on the other. The new CSPECT Scanner is formed by combining the SPECT scanner and the CT scanner and new software is added to accomplish what neither scanner could do alone. By combining the SPECT scanner and the CT scanner a new instrument, the combined CSPECT Scanner is formed. Two gantries, one for SPECT and the other for CT, are used but only a single table, which holds the patient in a fixed position, and a single computer are required to perform both studies. The CT study is not done for diagnostic purposes, but is done instead to obtain a map with which to convolve the acquired SPECT data. By collecting both data almost simultaneously, with the patient in the same position on the table for both studies, the computer can be made to convolve, add fuse or superimpose the radionuclide concentration information from SPECT data directly with the anatomical information obtained from the CT data. The SPECT results are used to shade, or color, or even obtain color shaded relief images of the anatomical information obtained by CT analysis.

The new combined CSPECT Scanner significantly improves the nuclear medicine physician's ability to accurately interpret radionuclide distribution information. In addition, this new technology will assist the radiolabeled monoclonal antibody research and development. Together these complimentary technologies will dramatically change the current practice of nuclear medicine.

Referring to the drawing in order to demonstrate the present invention. There is sketched in the FIG. 1 a generalized view of the combined CSPECT Scanner 10 of the invention. The combined CSPECT Scanner 10 includes the gantry supporting the CT scanner 12 adjacently aligned with the gantry supporting the SPECT Scanner 14 to obtain the required CT data and acquired SPECT information. A single combined CT and SPECT gantry may also be used.

A single table 16 is positioned to sequentially pass through both gantries. A patient is positioned on the table in a fixed position and slides through the gantries. Initially, the CT data is obtained. Next, the SPECT data is collected. A single computer 18 mathematically convolves the two image data sets. The CT data is processed to provide a background (map) upon which to more or less superimpose the SPECT data. The CT anatomical data is thus convolved with the SPECT radioisotope distribution data to provide a color shaded relief image.

A single computer 18, preferably SUN SPARC-10, DEC Alpha, or Intel Pentium is used for analysis. There are four video display terminals although a single video display may be all that is necessary. Shown to display information are the machine control display terminal 20, the raw CT display terminal 22, the raw SPECT display terminal 24 and the combined single photon emission computed tomography CSPECT display terminal 26. It is the presentation of the data on the CSPECT display terminal 26 that is the most important element of the invention.

The CT anatomical data is convolved with the SPECT radioisotope distribution data to provide the color shaded relief image. The image is then printed on a color laser film printer 28 or other suitable hard copy output device. Soft copies could alternately be provided at a cost savings if applicable. Many different types of hard copy output are available including a modern color laser plain paper printer or a color video printer. Image resolution is deemed to be sufficient at 512×512 pixels per cross-sectional image slice.

As pointed out, the FIG. 1 shows four display terminals 20, 22, 24 and 26. However any number of computer display terminals can be provided depending upon the requirements. In the present situation, display terminal 20 controls the computer, display terminal 22 displays the premerged CT data, display terminal 24 displays the naked SPECT data, and display terminal 26 displays the combined SPECT and CT image data. It is the ability to combine the two image sets in a meaningful way that is the prime thrust of the invention. This ability is obtained by controlling all of the variables associated with image acquisition, and obtaining the image data sets with the patient in a fixed position. This is accomplished when both sets of data are collected almost simultaneously while the patient is in the fixed position. The mathematics associated with combining the images is a trivial exercise. The exact method of analysis and display is within the state of the art. In fact many various modes of display would be provided with the interpreting physician choosing the preferred image analysis in a given situation.

It will be understood by those skilled in the art, that various modifications may be made without departing from the spirit and scope of the invention.

What is claimed is:

1. A combined imaging scanner comprising, in combination,
    a first separate gantry supported computed tomographic CT scanner adjacently axially aligned with a second separate gantry supported single photon emission computed tomographic SPECT scanner, and
    a computer for superimposing radioisotope distribution data from the SPECT scanner onto anatomical data from the CT scanner.

2. A combined imaging scanner according to claim 1 comprising a printer in combination with said computer.

3. A combined imaging scanner according to claim 2 comprising a table in combination with said CT and SPECT scanners.

4. A combined imaging scanner according to claim 3 wherein said table is capable of holding a person in a fixed position.

5. A combined imaging scanner according to claim 4 wherein said table slides through said first and second gantries sequentially.

6. A combined imaging scanner according to claim 5 wherein the CT anatomical data is convolved with the SPECT radioisotope distribution data.

7. A combined imaging scanner according to claim 6 wherein the CT anatomical data provides a background map for the SPECT radioisotope distribution data.

* * * * *